United States Patent [19]

Selva et al.

[11] Patent Number: 5,514,649
[45] Date of Patent: May 7, 1996

[54] ANTIBIOTIC GE 2270 FACTORS $C_{2A}$

[75] Inventors: Enrico Selva, Gropello Cairoli; Sergio Stella, Poggibonsi; Luigi Colombo, Malnate; Maurizio Denaro, Opera, all of Italy

[73] Assignee: Gruppo Lepetit S.p.A., Gerenzano, Italy

[21] Appl. No.: 428,787

[22] Filed: Apr. 21, 1995

Related U.S. Application Data

[63] Continuation of Ser. No. 931,084, Aug. 17, 1992, abandoned.

[30] Foreign Application Priority Data

Aug. 30, 1991 [EP] European Pat. Off. ............ 91114667

[51] Int. Cl.6 .................. C07K 5/00; C07K 7/00; A61K 38/00; A61K 35/00
[52] U.S. Cl. .................. 514/9; 514/11; 514/18; 424/115; 424/116; 424/117; 424/123

[58] Field of Search ................ 514/9, 11, 18; 424/115, 116, 117, 123, 124

[56] References Cited

U.S. PATENT DOCUMENTS

| 5,139,778 | 8/1992 | Selva et al. | 424/117 |
| 5,202,241 | 4/1993 | Selva et al. | 435/71.3 |

FOREIGN PATENT DOCUMENTS

| 0359062 | 3/1990 | European Pat. Off. . |
| 0451486 | 10/1991 | European Pat. Off. . |

*Primary Examiner*—Jill Warden
*Assistant Examiner*—A. M. Davenport
*Attorney, Agent, or Firm*—J. Michael Dixon

[57] ABSTRACT

The present invention is directed to a new antibiotic substance denominated antibiotic GE 2270 factor $C_{2a}$, the addition salts thereof, the pharmaceutical compositions thereof and its use as medicament, particularly in the treatment of infectious diseases involving microorganisms susceptible to it and its use as animal growth promoter.

6 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: circular ( i i ) MOLECULE TYPE: peptide ( x i ) SEQUENCE DESCRIPTION: SEQ ID NO:1:

Gly Xaa Xaa Xaa
1

ANTIBIOTIC GE 2270 FACTORS $C_{2A}$

CROSS-REFERENCE TO RELATED APPLICATION

This is a continuation of application Ser. No. 07/931,084, filed Aug. 17. 1992 now abandoned, which is herein incorporated by reference.

The present invention is directed to a new antibiotic substance denominated antibiotic GE 2270 factor $C_{2a}$, the addition salts thereof, the pharmaceutical compositions thereof and its use as medicament, particularly in the treatment of infectious diseases involving microorganisms susceptible to it.

The compound of the invention is isolated from the cultures of *Planobispora rosea* ATCC 53773 or an antibiotic GE 2270 producing variant or mutant thereof capable of producing factor $C_{2a}$. In particular, it is found in the mycelium and also in the fermentation broths of the cultured microorganism.

*Planobispora rosea* ATCC 53773 was isolated from a soil sample which was deposited on Jun. 14, 1988 with the American Type Culture Collection (ATCC), 12301 Parklawn Drive, Rockville, Md. 20852 Maryland, U.S.A., under the provisions of the Budapest Treaty.

The strain has been accorded accession number ATCC 53773.

This strain was already described in European Patent Application Publication No. 359062 in connection with the preparation of a new antibiotic substance named antibiotic GE 2270 factor A.

The compound of the invention is produced by the above named microbial strain together with antibiotic GE 2270 factor A, which is normally the most abundant fraction, and with antibiotic GE 2270 factors $B_1$, $B_2$, $C_1$, $C_2$, $D_1$, $D_2$, E and T which are described in the European Patent Application Publication No. 451486 corresponding to U.S. patent application Ser. No. 856,857, both claiming the priority of Mar. 8, 1990 and Oct. 22, 1990, European Patent Applications Serial No. 90104409.9 and Serial No. 90120214.3, respectively.

The production of antibiotic GE 2270 factor $C_{2a}$ is achieved by cultivating a Planobispora strain capable of producing it, i.e. *Planobispora rosea* ATCC 53773 or an antibiotic GE 2270 producing variant or mutant thereof capable of producing factor $C_{2a}$, under aerobic conditions in an aqueous nutrient medium containing assimilable sources of carbon, nitrogen, and inorganic salts. Many of the nutrient media usually employed in the fermentation art can be used, however certain media are preferred. Preferred carbon sources are glucose, mannose, galactose, starch, corn meal and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, magnesium, calcium, ammonium, chloride, carbonate sulfate, phosphate, nitrate and the like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed. The antibiotic GE 2270 producing strain can be grown at temperatures between 20° and 40° C., preferably between 24° and 35° C.

During fermentation, the antibiotic production can be monitored by testing broth or mycelial extract samples for antibiotic activity for instance by bioassays or TLC or HPLC procedures.

Sensitive organisms to antibiotic GE 2270 factor $C_{2a}$ such as *Bacillus subtilis* and *S. aureus* can be used as test organisms. The bioassay is conveniently performed by the agar diffusion method on agar plates. Maximum production of antibiotic activity generally occurs between the second and the eighth day of fermentation.

Antibiotic GE 2270 factor $C_{2a}$ is produced by cultivating the strain *Planobispora rosea* ATCC 53773, or an antibiotic GE 2270 producing mutant or variant thereof capable of producing factor $C_{2a}$, and is mainly found in the mycelium even if a certain amount of product can be isolated from the fermentation broth.

The morphological, physiological and chemotaxonomical characteristics of the strain *Planobispora rosea* ATCC 53773 are described in the above mentioned EP-A 359062.

As with other microorganisms, the characteristics of the antibiotic GE 2270 factor $C_{2a}$ producing strains are subject to variation. For example, artificial variants and mutants of the strain can be obtained by treatment with various known mutagens, such as U.V. rays, X-rays, high frequency waves, radioactive rays, and chemicals such as nitrous acid, N-methyl-N'-nitro-N-nitroso-guanidine, and many others. All natural and artificial variants and mutants which belong to a species of the genus Planobispora and produce antibiotic GE 2270 factor $C_{2a}$ are deemed equivalent to strain *Planobispora rosea* ATCC 53773 for the purposes of this invention.

As mentioned above, antibiotic GE 2270 factor $C_{2a}$ is generally found mainly in the mycelium of the producing strain, while a minor amount of substance is found also in the fermentation broth.

RECOVERY AND ISOLATION OF THE ANTIBIOTIC OF THE INVENTION

The recovery of antibiotic GE 2270 factor $C_{2a}$ from the mycelium or the fermentation broths of the producing microorganism is conducted according to known per se techniques such as extraction with solvents, precipitation by adding non-solvents or by changing the pH of the solution, partition chromatography, adsorption chromatography, reverse-phase partition chromatography, ion-exchange chromatography, molecular exclusion chromatography and the like.

A preferred procedure for recovering the antibiotic substance of the invention from the mycelium includes extracting the filtered or centrifugated mycelium with a water-miscible organic solvent, concentrating the extracts and recovering the crude antibiotic substance by precipitation, optionally with the addition of a precipitating agent, by extraction of the aqueous residue with a water-immiscible organic solvent or by adsorption chromatography followed by elution of the desired product from the absorption matrix.

A preferred procedure for recovering the antibiotic of the invention from the fermentation broth includes extraction with a water-immiscible organic solvent, followed by precipitation from the concentrated extracts, possibly by adding a precipitating agent, or by further extraction of an aqueous residue thereof with a water-immiscible solvent. Alternatively, the fermentation broth can be contacted with an adsorption matrix followed by elution with a polar elution mixture. This chromatographic procedure can also be applied to a concentrated extract obtained from the fermentation broth instead of on the broth itself.

The term "water-miscible solvent" as used in this application, is intended to have the meaning currently given in the art to this term and refers to solvents that, at the conditions of use, are miscible with water in a reasonably wide concentration range.

Examples of water-miscible organic solvents that can be used in the extraction of the antibiotic substance of the invention from the mycelial mass are: lower alkanols, e.g. ($C_1$–$C_3$)alkanols such as methanol, ethanol and propanol; lower ketones, e.g. ($C_3$–$C_4$)ketones such as acetone and ethylmethylketone; cyclic ethers such as dioxane and tetrahydrofuran; glycols and their products of partial etherification, such as ethylene glycol, propylene glycol and ethylene glycol monomethyl ether; lower amides such as dimethylformamide, diethylformamide; and dimethylsulfoxide.

The term "water-immiscible solvent" as used in this application, is intended to have the meaning currently given in the art to this term and refers to solvents that at the conditions of use are slightly miscible or practically immiscible with water in a reasonably wide concentration range, suitable for the intended use.

Examples of water-immiscible organic solvents that can be used in the extraction of the antibiotic substance of the invention from the fermentation broth are: the usual hydrocarbon solvents which may be linear, branched or cyclic such as hexane or cyclohexane; halogenated hydrocarbons such as chloroform, carbon tetrachloride, dichloroethane, fluorobromoethane, dibromoethane, trichloropropane, chlorotrifluorooctane and the like; aromatic hydrocarbons such as benzene, toluene, xylene and the like; esters of at least four carbon atoms, such as ethyl acetate, propyl acetate, ethyl butyrrate, and the like; alkanols of at least four carbon atoms which may be linear, branched or cyclic such as butanol, 1-pentanol, 2-pentanol, 3-pentanol, 1-hexanol, 2-hexanol, 3-hexanol, 3,3-dimethyl-1-butanol, 4-methyl-1-pentanol; 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopentyl-1-propanol, cyclohexanol, cycloheptanol, cyclooctanol, 2,3-dimethylcyclohexanol, 4-ethylcyclohexanol, cyclooctylmethanol, 6-methyl-5-hepten-2-ol, 1-nonanol, 2-nonanol, 1-decanol, 2-decanol and 3-decanol; straight or branched alkyl ethers and mixture thereof such as ethyl ether, propyl ether, butyl ether, etc; and mixtures or functional derivatives thereof.

As known in the art, product extraction may be improved by salting the aqueous phase containing said product.

When, following an extraction operation, an aqueous phase is recovered containing a substantial amount of an organic solvent, it may be convenient to azeotropically distill water from it. Generally, this requires adding a solvent capable of forming minimum azeotropic mixtures with water, followed by the addition of a precipitating agent to precipitate the desired product, if necessary. Representative examples of organic solvents capable of forming minimum azeotropic mixtures with water are n-butanol, benzene, toluene, butyl ether, carbon tetrachloride, chloroform, cyclohexane, 2,5-dimethylfurane, hexane and m-xylene; the preferred solvent being n-butanol.

Examples of precipitating agents are petroleum ether, lower alkyl ethers, such as ethyl ether, propyl ether and butyl ether, and lower alkyl ketones such as acetone.

After recovery of the crude mixture as described above, it might be necessary to submit it to a further purification/concentration step before separating the single antibiotic substance of the invention. A chromatographic procedure is the first choice, in this case.

As mentioned above, antibiotic GE 2270 factor $C_{2a}$ of the invention is normally co-produced with antibiotic GE 2270 factors A, $B_1$, $B_2$, $C_1$, $C_2$, $D_1$, $D_2$, E and T. Therefore, it is generally necessary to separate factor $C_{2a}$ from the major factor (i.e. factor A) and the other factors produced in minor quantity (i.e. factors $B_1$, $B_2$, $C_1$, $C_2$, $D_1$, $D_2$, E and T).

In general, the crude mixture recovered from fermentation is submitted to purification to obtain a purified mixture containing antibiotic GE 2270 factor $C_{2a}$ together with some amounts of the other factors. This material is then further purified to yield the pure substance of the invention.

Examples of chromatographic systems that can be conveniently used in the first purification step mentioned above are polystyrene or mixed polystyrenedivinylbenzene resins such as Amberlite® XAD2 or XAD4 (Rohm and Haas), Dowex® S112 (Dow Chemical Co.) and Diaion® HP 20 (Mitsubishi); acrylic resins such as XAD7 or XAD8 (Rohm and Haas); polyamides such as polycaprolactames, nylons and cross-linked polyvinylpyrrolidones generally having a pore volume (ml/g) ranging between 1 and 5, surface area ($m^2$/g) ranging between 1 and 100, apparent density (g/ml) ranging between 0.15 and 0.50, average pore diameter (Angstrom units) ranging between 100 and 3000 and particles size distribution where at least 40 percent of the particle size is lower than 300 micrometers, such as Polyamide-CC 6, Polyamide-SC 6, Polyamide-CC 6.6, Polyamide-CC 6AC and Polyamide-SC 6AC (Macherey-Nagel & Co., West Germany), the polyvinylpyrrolidone resin PVP-CL (Aldrich Chemie GmbH & Co., KG, West Germany), the polyamide resin PA 400 (M. Woelm AG, West Germany); and carbon.

In the case of polystyrene or acrylic resin a preferred eluent is a polar solvent mixture of water-miscible solvents such as those reported above; in the case of a polyamide resin the eluent is preferably an aqueous mixture of a water-miscible solvent, such as the ones mentioned above, while for carbon a preferred eluent is a lower ketone such as acetone or a lower alcohol such as methanol.

Further chromatographic procedures that can be conveniently used in the step mentioned above include also chromatography on stationary phases such as silica gel, allumina, diatomaceous earth and the like, with an organic eluting phase made of solvents including halogenated lower hydrocarbons, lower alkanols, ethers, and higher ketones of the type already mentioned above and mixtures thereof.

Conveniently, also the so-called steric exclusion chromatography can be employed with good purification results. In particular, controlled pore cross-linked dextrans in which most of the hydroxyl groups have been alkylated, e.g. Sephadex LH-20 (Pharmacia Fine Chemicals, Ab), are usefully employed in this case.

If necessary, the above mentioned procedures can be repeated and/or combined.

According to the ordinary procedures described above, it is usually obtained a purified mixture which, beyond the invention compound, may still contain some amounts of antibiotic GE $_{2270}$ factors A, $B_1$, $B_2$, $C_1$, $C_2$, $D_1$, $D_2$, E and T.

Separation of antibiotic GE 2270 factor $C_{2a}$ from the purified mixture can be done by means of procedures which are generally selected from the chromatographic techniques, such as those mentioned above. However, reverse-phase chromatography appears to be a preferred separation technique. In addition to conventional reverse-phase column chromatography, also preparative HPLC using a reverse-phase column is usefully employed.

The stationary phase in this chromatographic technique may be, for instance, silanized silica gel having various functional derivatizations and the eluent may be an aqueous mixture of water-miscible solvents of the kind mentioned above.

Examples of functionalized silanized silica gels are those bearing ($C_8$–$C_{22}$)alkyl groups, such as those wherein the functionality is represented by e.g. octadecylsilane or octylsilane moieties, or cyclohexane, phenyl, and similar functions. These resins are commercially available and new additions are regularly registered having similar or even improved properties that can be usefully employed in the process of the invention.

A specifically preferred preparative HPLC technique employs an octadecyl functionalized silica gel and an eluting mixture containing acetonitrile, tetrahydrofuran and aqueous ammonium formate.

A specifically preferred elution mode is represented by an elution with linear gradient of phase A and phase B from about 40% to about 50% of phase A, wherein phase A is a mixture of acetonitrile:tetrahydrofuran:40 mM ammonium formate, 40:40:20 and phase B is a mixture of the same components but in proportion 10:10:80.

Fractions are collected as usual according to their content, e.g. by following the elution profile with a conventional U.V. detector at 254 nm, the solvents are then removed according to known per se techniques (e.g. evaporation under reduced pressure, lyophilization etc.) to isolate the pure antibiotic of the invention which, optionally, may be further purified from the salts present in the eluting phases, for instance, by absorption on a polystyrene or mixed polystyrene-divinylbenzene resin followed by washing out the salts with distilled water and elution of the antibiotic with a water mixable solvent and/or may be crystallized from lower alkanols such as methanol, ethanol, propanol and isopropanol.

As usual in this art, the production as well as the recovery and purification steps may be monitored by a variety of analytical procedures including bioassays such as paper disc or agar diffusion assays on sensible microorganisms, TLC or HPLC procedures, which may involve a UV or microbial detection step.

A preferred HPLC analytical technique is represented by a reverse-phase HPLC using a column with porous and spheric particles of silanized silica gel, e.g. silica gel functionalized with C-8 alkyl groups having a uniform diameter (such as 5 micrometer Bakerbond® C8, Baker Research Products, U.S.A.) and an eluent which is a linear gradient mixture of a polar water miscible solvent, such as those described above with a gradient of increasing polarity.

In this case a preferred elution mixture is the following:

Phase A: $CH_3CN$:tetrahydrofuran:40 mM $HCOONH_4$, 40:40:20

Phase B: $CH_3CN$:tetrahydrofuran:40 mM $HCOONH_4$, 10:10:80, while a preferred elution mode is represented by a linear gradient from 20% to 30% of phase A in phase B in about 20 min, with a flow rate of about 1.8 ml/min and UV detection at 254 nm.

Figure 1:
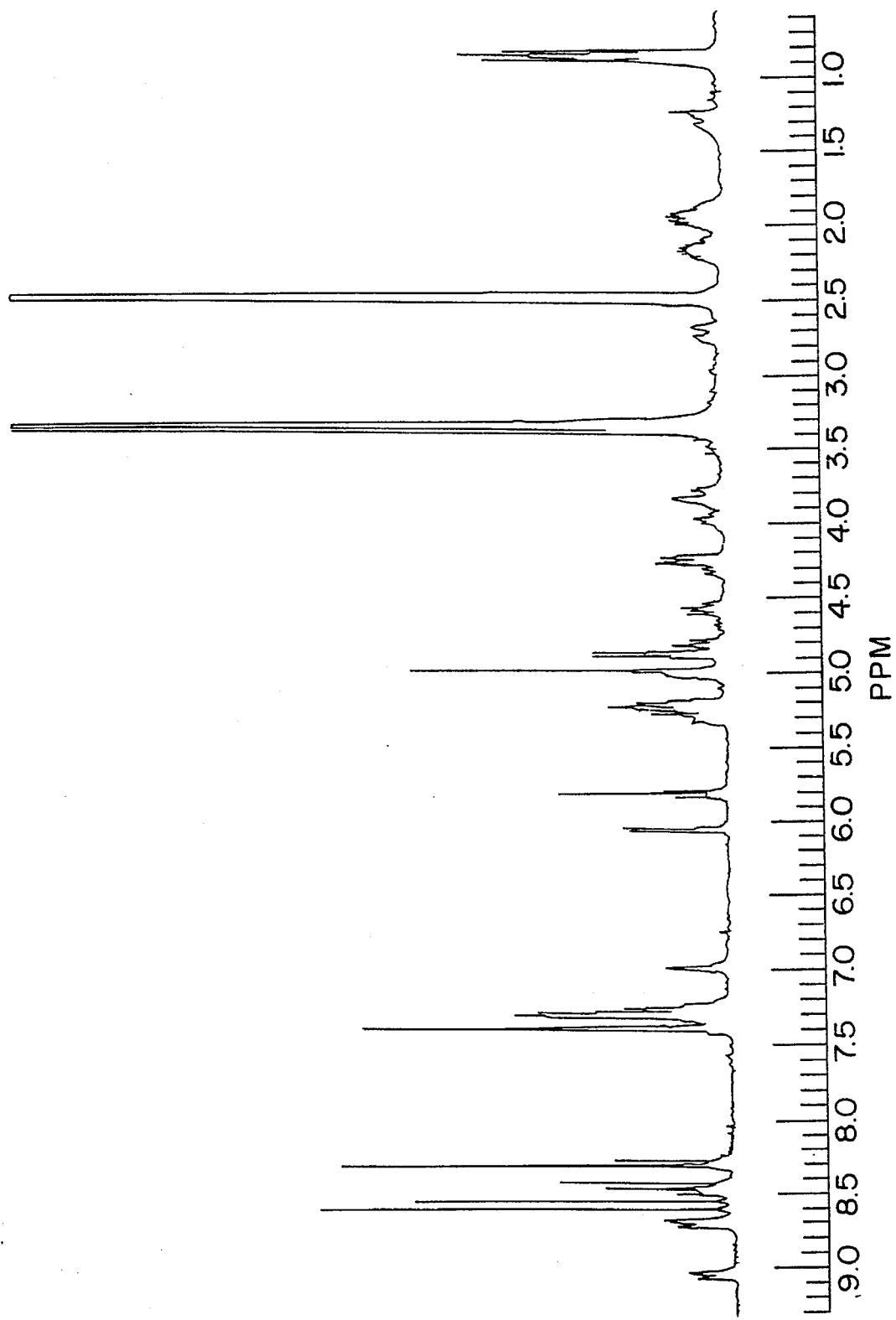
FIG. 1 shows the $^1$H-NMR specturm of antibiotic GE 2270 factor $C_{2a}$.

PHYSICO-CHEMICAL CHARACTERISTICS OF ANTIBIOTIC GE 2270 $C_{2a}$:

A) The ultraviolet absorption spectrum recorded with a Perkin Elmer Model 320 spectrometer exhibit the following absorption maxima:

| Solvent | UV max (nm) |
| --- | --- |
| 0.1 M HCl | 245–250 (shoulder) |
| | 300–315 |
| 0.1 M KOH | 245–250 (shoulder) |
| | 300–315 |
| Phosphate buffer pH 7.38 | 245–250 (shoulder) |
| | 300–315 |
| Methanol | 245–250 (shoulder) |
| | 300–315 |

B) The $^1$H-NMR spectrum of antibiotic GE 2270 factor $C_{2a}$ was recorded at 250 MHz with a Bruker spectrometer. The spectrum of the antibiotic in DMSO-$d_6$ (hexadeuterodimethylsulfoxide) using TMS as the internal standard (0.00 ppm) exhibits the following groups of signals [δ, ppm, m] (s=singlet, d=doublet, t=triplet, m=multiplet, Py=pyridine, Tz=thiazole) 9.03, d, (NH); 8.70, d, (2NH's); 8.60, s, 8.54, s, 8.29, s, and 7.38, s, (Tz CH's); 8.48, m, (glycine NH); 8.43, d, and 8.27, d, (Py CH's); 7.35–7.20, m, (aromatic CH's and primary amide NH); 6.98, s (primary amide NH); 6.04, d, (OH); 5.80, t (OH); 5.35–5.15, m, (αCH's); 5.04, m, (phenylserine βCH); 4.98, s [$CH_2(OCH_3)$]; 4.87, d, [$CH_2(OH)$]; 4.81, m and 4.56, m, (oxazoline $CH_2$); 4.35–3.75, m, ($CH_2$ of glycine and prolineamide CH's); 3.39,s, ($OCH_3$); 2.71, m, and 1.30, m, ($CH_2$ of asparagine); 2.48, d, ($NCH_3$ of N-methylasparagine); 2.22–1.80, m, (isopropyl CH and prolineamide CH's); 0.88 and 0.84, d, (valine $CH_3$'s)

FIG. 1 shows the $^1$H-NMR spectrum of antibiotic GE 2270 factor $C_{2a}$.

c) Antibiotic GE 2270 factor $C_{2a}$ shows retention time ($R_t$) of 12.6 min and retention time relative to antibiotic GE 2270 factor A ($R_t$ 16.6 min) of 0.76 when analyzed with the following reverse phase HPLC system: Column: Bakerbond® C8 (5 μm) 4.6×250 mm (Bakerbond® is a trade name for reverse phase octylsilyl silica gel HPLC columns supplied by J. T. Baker Research Product, Phillisburg, N.J. 08865 USA)

Flow rate: 1.8 ml/min

Phase A: $CH_3CN$:tetrahydrofuran:40 mM $HCOONH_4$ 40:40:20

Phase B: $CH_3CN$:tetrahydrofuran:40 mM $HCOONH_4$ 10:10:80

Elution: linear gradient from 20% to 30% of Phase A in 20 min

Detection: UV 254 nm D) The main FAB-MS peak of antibiotic GE 2270 factor $C_{2a}$ is 1306 daltons. This corresponds most likely to the lowest isotope of the protonated molecular ion. The analysis was performed on a Kratos MS-50 double focusing mass spectrometer, using 8 kV accelerating voltage and a saddle field atom gun with Xe gas ($2\times10^{-5}$ tort pressure indicated on the source ion guage) at 6 kV voltage and 1 mA current.

The antibiotic for the FAB-MS analysis was mixed with a thioglycerol matrix containing 0.1M acetic acid.

On the basis of the physico-chemical data reported above, the following structure formula can be tentatively assigned to antibiotic GE 2270 factor $C_{2a}$: Seq. No. 1: Gly Xaa Xaa Xaa.

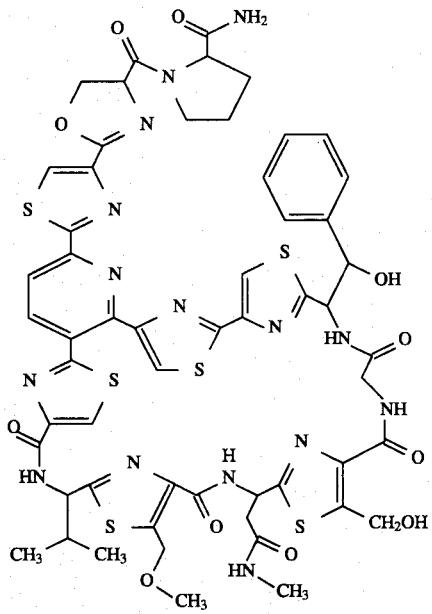

As it appears from the above formula, antibiotic GE 2270 factor $C_{2a}$ contains several heterocyclic bases portions that can form addition salts with acids, such as mineral and organic acids. In particular, salts with pharmaceutically acceptable acids are preferred.

The antimicrobial activity of antibiotic GE 2270 factor $C_{2a}$ can be demonstrated by a series of standard tests in vitro.

Minimal inhibitory concentrations (MIC) were determined by microbroth dilution methodology. Inocula were $10^4$–$10^5$ CFU per mL. All microorganisms were cultured at 37° C. MIC were read at 18–24 h, except for *Neisseria gonorrhoeae*, *Bacteroides fragilis*, and *Propionibacterium acnes* (48 h). *N. qonorrhoeae* was incubated in a 5% $CO_2$ atmosphere; anaerobes were incubated in an anaerobic gas mixture. Media used were: Oxoid Iso-Sensitest broth (staphylococci, *Enterococcus faecalis*, *Escherichia coli*, *Proteus vulgaris*, *Pseudomonas aeruginosa*); Difco Todd-Hewitt broth (streptococci); Difco GC base broth with 1% BBL IsoVitaleX for *N. gonorrhoeae*; Difco Wilkins-Chalgren broth for the anaerobes.

The minimal inhibitory concentrations (MIC, microgram/ml) of the antibiotic are reported below in Table I.

TABLE I

| In vitro activity of antibiotic GE 2270 factor $C_{2a}$ | |
|---|---|
| Strain | MIC (microgram/ml) |
| S. aureus L165 Tour | 4 |
| S. epidermidis L147 ATCC 12228 | 2 |
| S. haemolyticus L602 | 2 |
| S. pyogenes L49 C203 | 0.5 |
| S. pneumoniae L44 UC41 | 0.13 |
| E. faecalis L149 ATCC7080 | 1 |
| P. acnes L1014 ATCC6919 | 0.03 |
| B. fragilis L1010 ATCC23745 | >128 |

TABLE I-continued

| In vitro activity of antibiotic GE 2270 factor $C_{2a}$ | |
|---|---|
| Strain | MIC (microgram/ml) |
| N. gonorrhoeae L997 ISM68/126 | >128 |
| E. coli L47 SKF12140 | >128 |
| P. aeruginosa ATCC 10145 | >128 |
| P. vulgaris ATCC 881 | >128 |

In view of its properties, the compound of the invention can be used as active ingredient in the preparation of medicaments for human or animal treatment.

In particular, antibiotic GE 2270 factor $C_{2a}$ is an antimicrobial agent mainly active against Gram positive bacteria and Gram positive as well as Gram negative anaerobes. It has no cross-resistance with meticillin, aminoglycosides or glycopeptide antibiotics.

The main therapeutic indication of the antibiotic substance of the invention is the treatment of infections related to the presence of a microorganism susceptible to it.

The term "treatment" is intended to encompass prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixture with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

A preferred pharmaceutical formulation is represented by a formulation suitable for a topical application on an intact or damaged skin or mucous membrane. Examples of such formulations are powders, ointments, creams and lotions. The excipients in these formulations are the usual pharmaceutically acceptable vehicles such oleaginous ointment bases (e.g. cetyl esters wax, oleic acid, olive oil, paraffin, spermaceti, starch glycerite); absorbent ointment bases (e.g. anhydrous lanolin, hydrophilic petrolatum), emulsion ointment bases (e.g. cetyl alcohol, glyceryl monostearate, lanolin, stearic acid), water-soluble ointment bases (e.g. glycol ethers and their derivatives which include polyethylene glycols, poly(oxy- 1,2-ethanediyl)-alpha-hydro-omega-hydroxy-octadecanoate, polysorbates, and polyethylene glycols mono-stearates).

These formulations may contain other known excipients, such as preservatives and are prepared as known in the art and reported in reference handbooks such as Remington's Pharmaceutical Sciences, Seventeenth edition, 1985, Mack Publishing Co.

The compound of the invention can also be formulated into formulations suitable for parenteral administration according to precedures known per se in the art and reported in reference books such as the one mentioned above.

For instance, a compound of the invention is formulated with a solubilizing agent such as polypropylene glycol or dimethylacetamide and a surface-active agent such as polyoxyethylene sorbitan mono-oleate or polyethoxylated castor oil in sterile water for injection.

An example of a typical formulation for parenteral administration contains 10 mg of antibiotic GE 2270 factor $C_{2a}$ for ml of final preparation, 10–20% of a surface-active agent which may be a polyoxyethylene sorbitan fatty acid ester, a polyoxyethylene castor oil derivative or a polyoxyethylene hydrogenated castor oil derivative and 0–20%, and preferably 10–20% of a solubilizing agent such as propylene glycol, dimethylacetamide, dimethylformamide, ter-butyl-N-hydroxycarmabate, 1,2-, 1,3-, or 1,4-butanediol, ethyl oleate, tetrahydrofurfuryl-polyethylene-glycol 200, dimethylisosorbide, benzyl alcohol and the like. A preferred solubilizing agent is propylene glycol.

Polyoxyethylene sorbitan fatty acid esters are commercially available and some of them are traded under the trade name "Tween". They are also known with the non-proprietary name of "polysorbates". Examples of them are polysorbate 20, 21, 40, 60, 61, 65, 80, 81 and 85. Preferred for use in the formulations of the invention is polysorbate 80 (sorbitan mono-9-octadecenoate, poly(oxy-1,2-ethanediyl-)derivatives).

Polyoxyethylene castor oils and polyoxyethylene hydrogenated castor oils are also commercially available. Some of them are traded with the trade name "Cremophor". Examples of such compounds are those known as Cremophor® EL (polyethoxylated castor oil), Cremophor® RH 40 (polyethoxylated hydrogenated castor oil), Cremophor® RH 60 (PEG 60 hydrogenated castor oil) or Emulphor® EL-719 (polyoxyethylated vegetable oil).

Preferably, a formulation for injection should have a pH in the range of 7±0.5. If necessary, it might be advisable to adjust the pH of the preparation with a suitable buffering agent. Conveniently, TRIS (i.e.trihydroxymethylaminomethane) or phosphate can be used as buffering agents.

A preferred formulation for parenteral administration includes the following excipients: Cremophor® EL (polyoxyl 35 castor oil USP/NF) 20%, propylene glycol from 5 to 20%, preferably 10–20%.

Generally, these formulations can be prepared by dissolving the active ingredient into the organic solvent, then adding the surface active ingredient, and finally diluting to the desired volume with sterile water for injection.

Other excipients, such as preservative or stabilizing agents can be added as known in the art.

An example of a parenteral formulation is the following:

| | |
|---|---|
| antibiotic GE 2270 factor $C_{2a}$ | 10 mg |
| PEG 40 castor oil (Cremophor ® EL) | 0.2 ml |
| propylene glycol | 0.2 ml |
| methyl parahydroxybenzoate | 0.5 mg |
| propyl parahydroxybenzoate | 0.05 mg |
| water for injection q.s. | 1 ml |

Alternatively, the active ingredient may be prepared as a lyophilized powder for reconstitution before use.

If the lyophilized material is prepared starting from a mixture containing the active ingredient and the surfactant, such as polyethylene glycol 60 hydrogenated castor oil, it can conveniently be reconstituted with the aqueous medium alone, without addition of an organic solvent.

Optionally, a common lyophilization aid can be added, if necessary, to obtain a lyophilized material in powder form.

Preferably, all these formulations are used for i.v. administration in the treatment of any infection involving a microorganism susceptible to the antibiotic of the invention.

In the treatment of pseudomembranous colitis or other diseases attributable to the presence of anaerobes in the gastrointestinal tract, an effective dose of the compound of the invention may be administered orally in a suitable pharmaceutical form such as a capsule, a tablet or an aqueous suspension.

The dosage of the active ingredient depends on many factors which include type, age and conditions of the patient, specific active ingredient and formulation selected for the administration, administration schedule, etc.

In general, effective antimicrobial dosages are employed per single unit dosage form.

Repeated applications/administrations, e.g. from 2 to 6 times a day, are in general preferred. An effective dosage may be in general in the range 0.5–50 mg/kg body weight/day.

A preferred topic preparation is an ointment containing from 1% to 10% of a compound of the present invention.

Anyway, the prescribing physician will be able to determine the optimal dosage for a given patient in a given situation.

The following examples further illustrate the invention and have not to be interpreted as limiting it in any way.

EXAMPLE 1

Production of antibiotic GE 2270 factors by fermentation

A culture of *Planobispora rosea* ATCC 53773 grown on agar slant was inoculated into two 500 ml Erlenmeyer flasks containing 100 ml of seed medium (starch 2%, polipeptone 0.5%, yeast extract 0.3%, beef extract 0.2%, soybean meal 0.2%, calcium carbonate 0.1%, brought to pH 7.0 before sterilization). Three 500 ml Erlenmeyer flasks of seed medium were inoculated (5% inoculum) with the culture incubated at 28° C. for 96 hours on a rotary shaker (200 rpm).

The cultures of the three Erlenmeyer flasks were incubated at 28° C. for 72 hours on a rotary shaker (200 rpm) and then were inoculated into a 10 l jar-fermentor containing 6 l of the seed medium. After 72 hours incubation at 28° C., stirring at 900 rpm and aeration (about one standard liter of air per volume per minute), the culture was inoculated into a jar-fermentor containing 200 l of production medium (starch 2%, peptone 0.25%, hydrolyzed casein 0.25%, yeast extract 0.3%, beef extract 0.2%, soybean meal 0.2%, calcium carbonate 0.1%, adjusted to pH 7.4 before sterilization).

After 126 hours of fermentation at 28° C. with 180 rpm stirring and aeration (about 0.5 standard liter of air per volume per minute), the harvested broth contained the antibiotic of the invention together with the other GE 2270 factors.

EXAMPLE 2 a) Recovery of crude GE 2270 factors

The mycelium was collected from the harvested broth by filtration with Hyflo filter aid. The mycelium cake was extracted subsequently with 60 and 20 l of acetone and the pooled extracts were concentrated under reduced pressure. The crude antibiotic complex was separated from the water residue by centrifugation in a liquid-solid separator. The wet material was solubilized into 2-propanol and the solution was concentrated under reduced pressure to remove water. The crude antibiotic complex (50 g) precipitated from the concentrated residue. This crude complex contains a major quantity of antibiotic GE 2270 factor A along with antibiotic GE 2270 factor $C_{2a}$ and the other minor factors mentioned above.

b) Isolation of a purified mixture containing antibiotic GE 2270 factor $C_{2a}$ in mixture with other GE 2270 factors The preparations of crude GE 2270 factors from 6 repeated fermentations were pooled and stirred with 12 l of $CH_2Cl_2$: methanol (93:7). The insoluble material was removed by filtration and the solution, containing the antibiotic complex, was applied to a 13 kg (230–400 mesh) silica gel column equilibrated in $CH_2Cl_2$: methanol (93:7). Antibiotic GE 2270 factor $C_{2a}$ was eluted from the column by eluting with $CH_2Cl_2$: methanol (93:7). The fractions containing the antibiotic of the invention (HPLC analysis) were pooled, were concentrated under reduced pressure and were dried to yield 23.5 g of antibiotic GE 2270 factor $C_{2a}$ in mixture with other minor factors.

A portion (5.5 g) of this preparation was again purified by flash chromatography on a column containing 400 g of silica gel (230–400 mesh) equilibrated in methylene chloride ($CH_2Cl_2$). The column was developed first with methylene chloride (1 liter) and then sequentially with a series of mixtures of methylene chloride/methanol in the following ratios (v/v): 96/4 (3 liters); 94/6 (1 liter); 92/8 (2 liters); 90/10 (6 liters) and 88/12 (4 liters).

The fractions containing mainly GE 2270 factor $C_{2a}$ (HPLC analysis) were pooled and were concentrated. The antibiotic preparation (646 mg) was precipitated upon addition of petroleum ether.

EXAMPLE 3

Isolation of pure antibiotic GE 2270 factor $C_{2a}$

The purified mixture containing mainly antibiotic GE 2270 factor $C_{2a}$ was further purified by preparative HPLC from the above described preparation.

A portion of the above described preparation of the antibiotic (10 mg) was solubilized in 1 ml of Phase A ($CH_3CN$: tetrahydrofuran: 40 mM $HCOONH_4$-40:40:20) and 1 ml of Phase B ($CH_3CN$: tetrahydrofuran: 40 mM $HCOONH_4$-10:10:80) and was injected into a HPLC 250× 20 mm Hibar column (E. Merck; Darmstadt F. R. Germany) packed with 7 μm Nucleosil® C18 (silica gel functionalized with octadecylsilane groups) which was equilibrated with a mixture of 40% Phase A and 60% Phase B. The column was eluted at 15 ml/min flow rate with a 22 minutes linear gradient from 40% to 50% of Phase A. The UV detection was 254 nm. The fractions of 10 subsequent chromatographic runs containing the pure antibiotic of the invention were pooled and were concentrated under reduced pressure to eliminate $CH_3CN$. Antibiotic GE 2270 factor $C_{2a}$ precipitated from water. The precipitate was collected by centrifugation, was washed twice with distilled water and was dried under vacuum yielding 66 mg of the pure antibiotic.

We claim:
1. Antibiotic GE 2270 factor $C_{2a}$ having the following characteristics:

A) Ultraviolet absorption spectrum exhibiting the following absorption maxima:

| Solvent | UV max (nm) |
|---|---|
| 0.1 M HCl | 245–250 (shoulder) |
|  | 300–315 |
| 0.1 M KOH | 245–250 (shoulder) |
|  | 300–315 |
| Phosphate buffer pH 7.38 | 245–250 (shoulder) |
|  | 300–315 |
| Methanol | 245–250 (shoulder) |
|  | 300–315 |

B) $^1$H-NMR spectrum exhibiting the following groups of signals in DMSO-$d_6$ (hexadeuterodimethylsulfoxide) using TMS as the internal standard (0.00 ppm) [δ, ppm, m] (s=singlet, d=doublet, t=triplet, m=multiplet, Py=pyridine, Tz=thiazole) 9.03, d, (NS); 8.70, d, (2NH's); 8.60, s, 8.54, s, 8.29, s, and 7.38, s, (Tz CH's); 8.48, m, (glycine NH); 8.43, d, and 8.27, d, (Py CH's); 7.35–7.20, m, (aromatic CH's and primary amide NH); 6.98, s (primary amide NH); 6.04, d, (OH); 5.80, t (OH); 5.35–5.15, m, (αCH's); 5.04, m, (phenylserine βCH); 4.98, s [CH$_2$(OCH$_3$)]; 4.87, d, [CH$_2$(OH)]; 4.81, m and 4.56, m, (oxazoline CH$_2$); 4.35–3.75, m, (CH$_2$ of glycine and prolineamide CH's); 3.39,s, (OCH$_3$); 2.71, m, and 1.30, m, (CH$_2$ of asparagine); 2.48, d, (NCH$_3$ of N-methylasparagine); 2.22–1.80, m, (isopropyl CH and prolineamide CH's); 0.88 and 0.84, d, (valine CH$_3$'s);

C) Retention time (R$_t$) of 12.6 min and retention time relative to antibiotic GE 2270 factor A (R$_t$ 16.6 min) of 0.76 in the following reverse phase HPLC system:

Column: Bakerbond® C8 (5 μm) 4.6×250 mm Flow rate: 1.8 ml/min

Phase A: CH$_3$CN:tetrahydrofuran:40 mM HCOONH$_4$ 40:40:20

Phase B: CH$_3$CN:tetrahydrofuran:40 mM HCOONH$_4$ 10:10:80

Elution: linear gradient from 20% to 30% of Phase A in 20 min;

Detection: UV 254 nm

D) Main FAB-MS peak corresponding to the lowest isotope of the protonated molecular ion exhibiting a value of 1306 daltons when obtained on a Kratos MS-50 double focusing mass spectrometer, using 8 kV accelerating voltage and a saddle field atom gun with Xe gas (2×10$^{-5}$ tort pressure indicated on the source ion guage) at 6 kV voltage and 1 mA current, the sample being mixed with a thioglycerol matrix containing 0.1M acetic acid;

and its addition salts.

2. A compound of claim 1 having the following formula

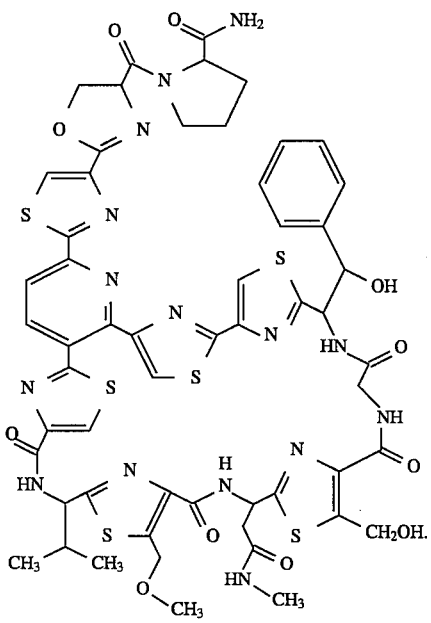

3. A pharmaceutical composition which contains the compound of claim 1 in admixture with a pharmaceutically acceptable carrier.

4. A pharmaceutical composition which contains the compound of claim 2 in admixture with a pharmaceutically acceptable carrier.

5. A method for the treatment of bacterial infections comprising administedring the compound in an effective amount according to claim 1 to a patient in need thereof.

6. A method for the treatmnet of bacterial infections comprising administering the compound in an effective amount according to claim 2 to a patient in need thereof.

* * * * *